US00PP13920P29

(12) United States Plant Patent
Trees

(10) Patent No.: US PP13,920 P2
(45) Date of Patent: Jul. 1, 2003

(54) ANGELONIA PLANT NAMED 'BALANGLAPI'

(75) Inventor: Scott C. Trees, Shell Beach, CA (US)

(73) Assignee: Ball Flora Plants, a division of Ball Horticultural Co., West Chicago, IL (US)

( * ) Notice: Subject to any disclaimer, the term of this patent is extended or adjusted under 35 U.S.C. 154(b) by 0 days.

(21) Appl. No.: 10/114,902

(22) Filed: Apr. 1, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Angelonia plant named 'Balanglapi', characterized by its upright, outwardly spreading and mounded plant habit; freely basal branching growth habit; and light violet-colored flowers.

1 Drawing Sheet

BOTANICAL CLASSIFICATION/CULTIVAR DENOMINATION

*Angelonia augustifolia* cultivar Balanglapi.

BACKGROUND OF THE INVENTION

The present Invention relates to a new and distinct cultivar of Angelonia plant, botanically known as *Angelonia augustifolia,* and hereinafter referred to by the name 'Balanglapi'.

The new Angelonia is a product of a planned breeding program conducted by the Inventor in Arroyo Grande, Calif. The objective of the breeding program is to develop new vigorous Angelonia cultivars that have a freely branching growth habit and numerous flowers with attractive coloration.

The new Angelonia originated from a cross-pollination made by the Inventor in 1999 of a proprietary *Angelonia augustifolia* selection identified as code number 142, not patented, as the female, or seed parent, with a proprietary *Angelonia augustifolia* selection identified as code number BFP-272, not patented, as the male, or pollen parent. The cultivar Balanglapi was discovered and selected by the Inventor as a flowering plant within the progeny of the stated cross-pollination in a controlled environment in Arroyo Grande, Calif.

Asexual reproduction of the new cultivar by terminal cuttings taken in Arroyo Grande, Calif. since June, 2000, has shown that the unique features of this new Angelonia are stable and reproduced true to type in successive generations.

SUMMARY OF THE INVENTION

The following traits have been repeatedly observed and are determined to be the unique characteristics of 'Balanglapi'. These characteristics in combination distinguish 'Balanglapi' as a new and distinct Angelonia cultivar:

1. Upright, outwardly spreading and mounded plant habit.
2. Freely basal branching growth habit.
3. Light violet-colored flowers.

Plants of the new Angelonia differ primarily from plants of the parent selections in flower coloration.

Plants of the new Angelonia can be compared to plants of the cultivar Pandiana, not patented. In side-by-side comparisons conducted in West Chicago, Ill., plants of the new Angelonia differed from plants of the cultivar Pandiana in the following characteristics:

1. Plants of the new Angelonia had shorter flower racemes than plants of the cultivar Pandiana.
2. Plants of the new Angelonia had more flowers per raceme than plants of the cultivar Pandiana.
3. Plants of the new Angelonia had shorter pedicels than plants of the cultivar Pandiana.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs differ from the color values cited in the detailed botanical description which accurately describe the colors of the new Angelonia.

The photograph at the top of the sheet comprises a side perspective view of multiple flowering plants of 'Balanglapi' grown in a container.

The photograph at the bottom of the sheet comprises a close-up view of a typical flowering raceme of 'Balanglapi'.

DETAILED BOTANICAL DESCRIPTION

The cultivar Balanglapi has not been observed under all possible environmental conditions. The phenotype may vary somewhat with variations in environment such as temperature and light intensity without, however, any variance in genotype.

The aforementioned photograph and following observations and measurements describe plants grown in West Chicago, Ill., under commercial practice in a polycarbonate-covered greenhouse with day temperatures ranging from 20 to 24° C., night temperatures ranging from 16 to 20° C. and light levels ranging from 4,000 to 6,000 footcandles. Rooted young plants were planted in containers and had been growing for about eight to ten weeks when the photographs and the description were taken.

In the following description, color references are made to The Royal Horticultural Society Colour Chart, 1995 Edition, except where general terms of ordinary dictionary significance are used.

Botanical classification: *Angelonia augustifolia* cultivar Balanglapi.

Parentage:

*Female parent.*—Proprietary *Angelonia augustifolia* selection identified as code number 142, not patented.

*Male parent.*—Proprietary *Angelonia augustifolia* selection identified as code number BFP-272, not patented.

Propagation:

*Type cutting.*—Terminal cuttings.

*Time to initiate roots.*—About 7 days at 18° C.

*Time to produce a rooted cutting.*—About 21 days at 18° C.

*Root description.*—Fibrous and white in color.

*Rooting habit.*—Freely branching.

Plant description:

*General appearance.*—Upright, outwardly spreading and mounded plant habit; freely basal branching growth habit, about six flowering branches form per plant. Moderately vigorous.

*Plant height.*—About 44.3 cm.

*Plant diameter or spread.*—About 49.5 cm.

*Stem texture.*—Smooth, glabrous.

*Stem color.*—145A.

*Foliage description.*—Arrangement: Opposite, simple; sessile. Length: About 5.7 cm. Width: About 1.4 cm. Shape: Lanceolate. Apex: Acute. Base: Obtuse. Margin: Serrate. Texture, upper surface: Smooth, glabrous. Texture, lower surface: Sparsely pubescent. Venation pattern: Pinnate. Color: Young and fully expanded foliage, upper surface: Darker than 137A; venation, 143C. Young and fully expanded foliage, lower surface: 137B; venation, 143C.

Flower description:

*Flower type and flowering habit.*—Single bi-labiate arranged on axillary racemes; flowers opposite. Usually about 19 open flowers per raceme. Flowers face outward. Flowers self-cleaning. Slight sweet fragrance.

*Flower longevity.*—Flowers last about five to seven days on the plant.

*Flowering season.*—Flowering is continuous from spring until fall.

*Raceme length.*—About 19.7 cm.

*Flower diameter.*—About 2.1 cm by 1.9 cm.

*Flower tube length.*—About 8.8 mm.

*Flower buds.*—Length: About 4 mm. Diameter: About 4 mm. Shape: Spherical. Color: 70A to 70B.

*Petals.*—Quantity: Five per flower, fused at base. Shape: Obovate. Apex: Rounded. Margin: Entire. Texture, upper and lower surfaces: Smooth. Color: All petals, upper surface: 84B. All petals, lower surface: 84B. Palate: 155D. Throat: 78B with spots, 71A. Tube: 78C.

*Sepals.*—Quantity: Five per flower, fused at base. Length: About 3.5 mm. Width: About 1.5 mm. Shape: Roughly deltoid. Apex: Acute. Texture, upper and lower surfaces: Smooth, glabrous. Color, upper surface: More yellow than 137C; towards base, overlain with 187A. Color, lower surface: 143A.

*Pedicels.*—Length: About 9 mm. Diameter: Less than 1 mm. Strength: Strong; flexible. Angle: Acute. Texture: Pubescence. Color: 141A overlain with 187B.

*Reproductive organs.*—Androecium: Stamen quantity: Four per flower. Stamen length: About 5 mm. Filament color: 155D. Anther length: About 1.8 mm. Anther color: 86A. Pollen amount: Moderate. Pollen color: 13D. Gynoecium: Pistil quantity: One per flower. Pistil length: About 4.3 mm. Style length: About 2.7 mm. Style color: 155D. Stigma length: About 0.3 mm. Stigma color: 150D. Ovary length: About 1.3 mm. Ovary color: 144B.

*Seeds/fruits.*—Seed and fruit development has not been observed.

Disease/pest resistance: Plants of the new Angelonia have not been observed to be resistant to pathogens and pests common to Angelonia.

It is claimed:

1. A new and distinct cultivar of Angelonia plant named 'Balanglapi', as illustrated and described.

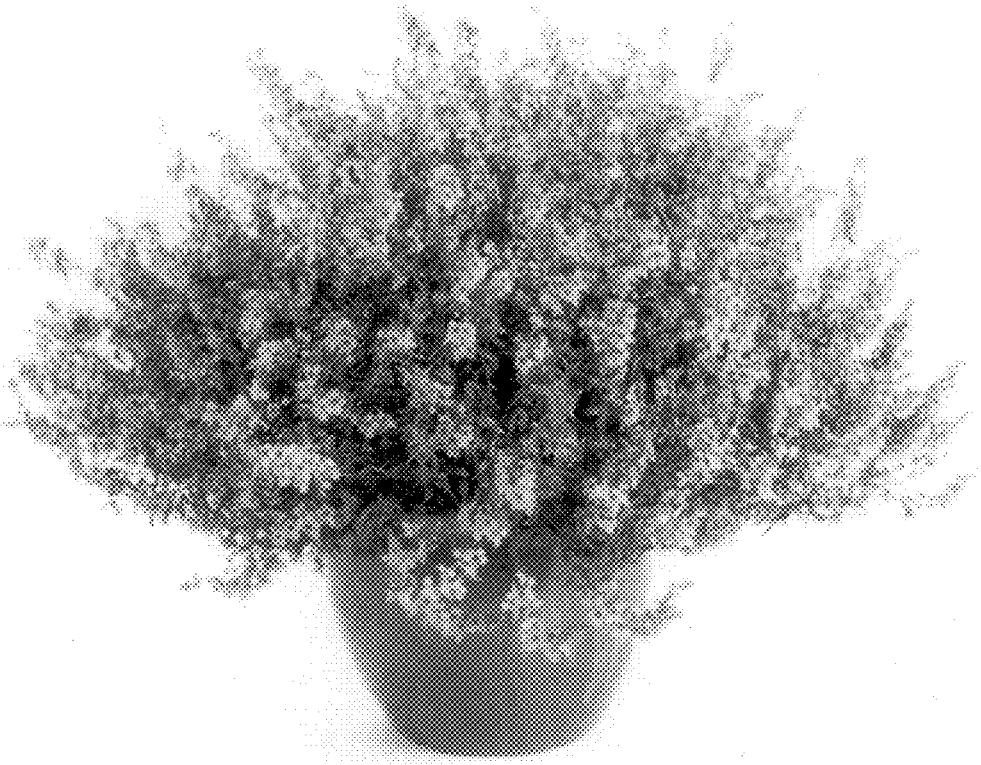
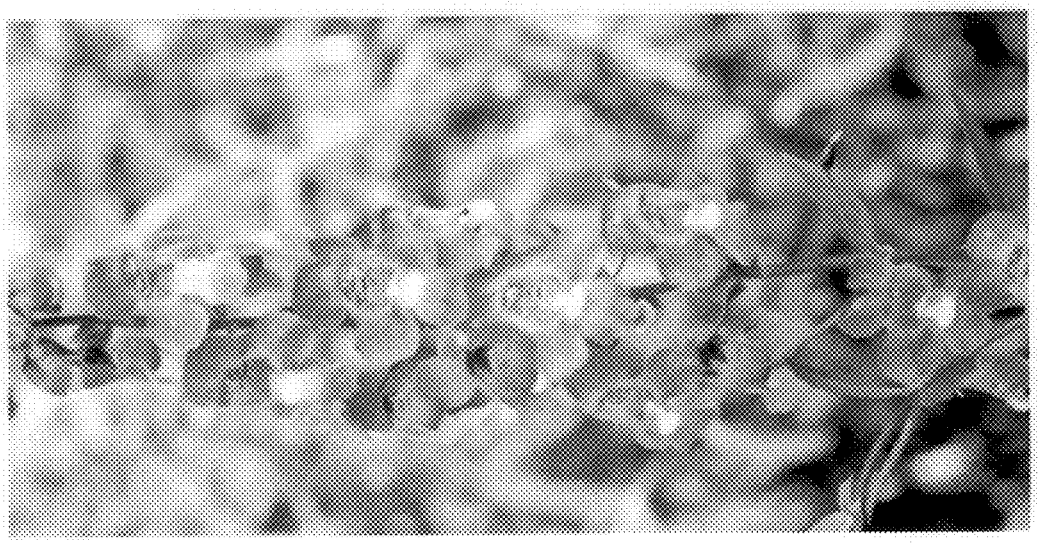

* * * * *